US00RE33858E

United States Patent [19]

Gropper et al.

[11] E Patent Number: Re. 33,858

[45] Reissued Date of Patent: Mar. 24, 1992

[54] APPARATUS FOR MEASURING A CHEMICAL ENTITY IN A LIQUID

[75] Inventors: Andrian Gropper, Cambridge; Richard Sidell, Needham; both of Mass.

[73] Assignee: Mallinckrodt Sensor Systems Inc., Ann Arbor, Mich.

[21] Appl. No.: 471,540

[22] Filed: Jan. 29, 1990

Related U.S. Patent Documents

Reissue of:

[64] Patent No.: 4,726,929
Issued: Feb. 23, 1988
Appl. No.: 41,650
Filed: Apr. 21, 1987

U.S. Applications:

[63] Continuation of Ser. No. 695,100, Jan. 25, 1985, abandoned.

[51] Int. Cl.[5] ..... G01N 1/10

[52] U.S. Cl. ..... 422/68.1; 422/82; 422/82.94; 422/100; 422/102; 356/244; 356/246

[58] Field of Search ..... 422/68.1, 81, 82, 100, 422/102, 82.04; 356/244, 246

[56] References Cited

U.S. PATENT DOCUMENTS

| | | | |
|---|---|---|---|
| Re. 28,801 | 5/1976 | Acker et al. | 422/58 X |
| 3,554,648 | 1/1971 | Boostrom et al. | 356/246 X |
| 3,842,679 | 10/1974 | Iwao et al. | 73/423 |
| 3,912,455 | 10/1975 | Lichtenstein et al. | 422/61 |
| 4,006,412 | 1/1978 | Johnson et al. | 324/96 |
| 4,119,406 | 10/1978 | Clemens | 422/68 X |
| 4,169,125 | 9/1979 | Rodriguez et al. | 422/68 X |
| 4,224,033 | 9/1980 | Hansen et al. | 422/82 X |
| 4,338,280 | 7/1982 | Ambers et al. | 422/68 |
| 4,390,499 | 6/1983 | Curtis et al. | 422/72 |
| 4,499,053 | 2/1985 | Jones | 422/68 |

OTHER PUBLICATIONS

Orion Model 1020 Na/K Brochure; Orion Research, Cambridge, Mass., ©1982.

*Primary Examiner*—Lynn Kummert
*Attorney, Agent, or Firm*—Krass & Young

[57] ABSTRACT

Apparatus for measuring or detecting a chemical entity in a liquid sample, the apparatus including a first module operationally connected to a second module, the first module having a flow passage for the sample, the flow passage including a sensor for measuring or detecting the chemical entity and *a* pump [means] for advancing the sample along the flow passage, the second module including [means] *an actuator* for actuating the pump means, and the second module being connected to the first module via [connecting means] *a connector* permitting disconnection of the first and second modules and connection of a replacement first module to the second module.

9 Claims, 4 Drawing Sheets

FIG 1
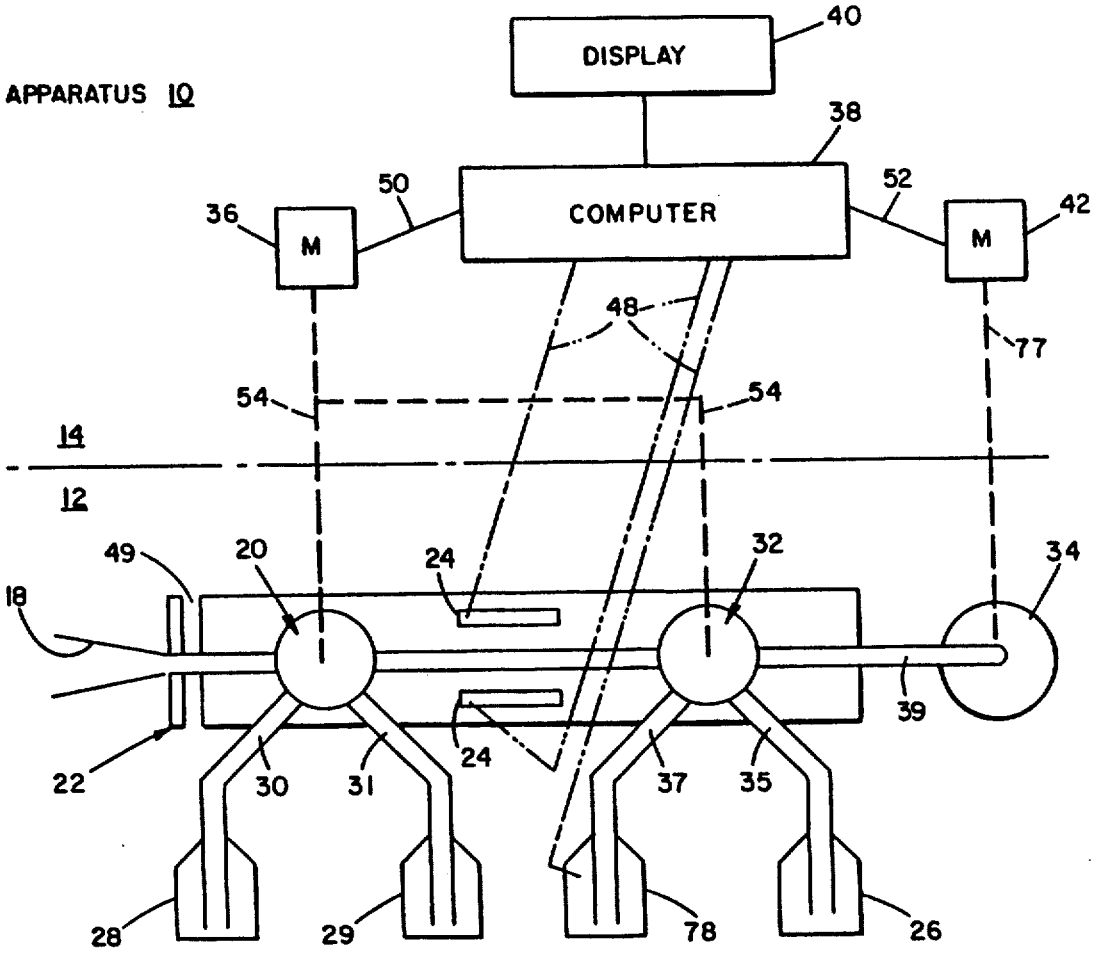
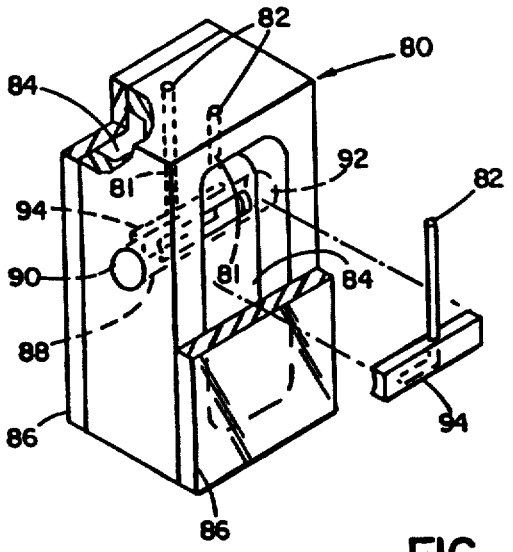
FIG 8

FIG 2
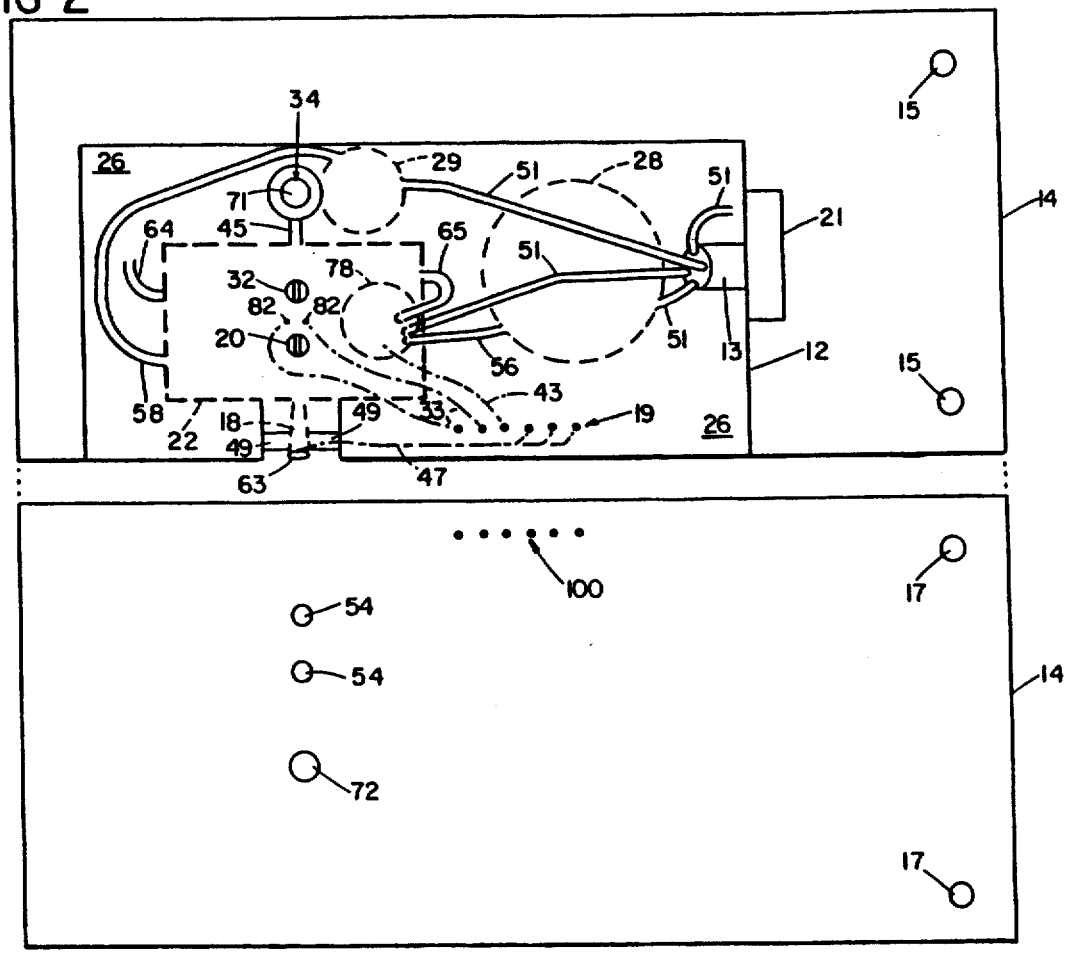
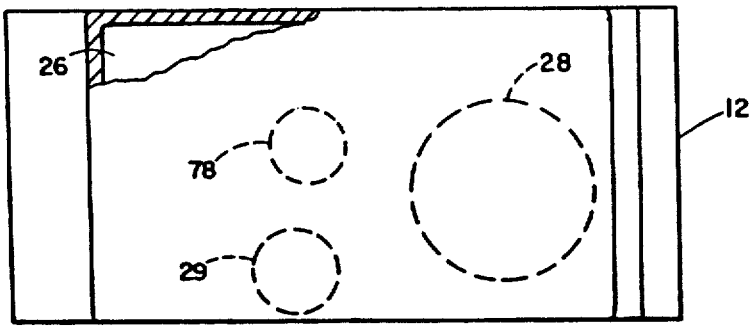
FIG 3
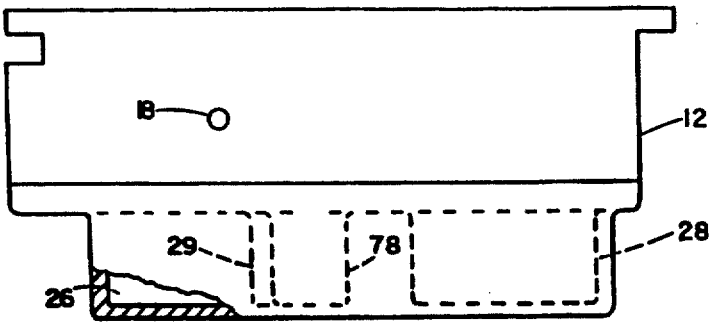
FIG 4

APPARATUS FOR MEASURING A CHEMICAL ENTITY IN A LIQUID

Matter enclosed in heavy brackets [ ] appears in the original patent but forms no part of this reissue specification; matter printed in italics indicates the additions made by reissue.

This application is a continuation of Ser. No. 695,100 filed Jan. 25, 1985, now abandoned.

BACKGROUND OF THE INVENTION

This invention relates to the measurement of chemical entities in liquid samples.

A wide variety of analytical systems are available for measuring chemical entities such as ions, e.g., potassium, sodium, and chloride; gases, e.g., $O_2$; and organic compounds, e.g., glucose, in liquid samples such as blood, urine, and liquids related to industrial processes. Such systems contain components which from time to time require maintenance or replacement.

SUMMARY OF THE INVENTION

In general, the invention features apparatus for measuring or detecting a chemical entity in a liquid sample, including a first module operationally connected to a second module, the first module having a flow passage for the sample including a sensor for measuring or detecting the chemical entity and pump means for advancing the sample along the flow passage, and the second module having means for actuating the pump means, the two modules being connected via means permitting disconnection and replacement of the first module.

In preferred embodiments, the sensor is capable of successively analyzing a plurality of samples; the first module includes a plurality of different sensors for measuring a plurality of different chemical entities in the sample; the pump means is located downstream from the sensor; and the first module further includes a waste chamber for holding the sample after the chemical entity has been measured, and a holding chamber for a calibrating reagent, whose passage into the flow passage is controlled by a selector valve which also controls intake of the sample into the flow passage, and which is actuated by means contained in the second module.

The flow-through apparatus of the invention provides all of the components which come into contact with the sample—the flow passage, sensors, and pump—as well as the depletable calibration reagent, in a sealed, disposable cartridge which, after it has been used to carry out a predetermined number of tests (e.g., sodium and potassium measurements on 100 whole blood or serum samples), is disposed of in its entirety and replaced. The user (e.g., a physician using the apparatus in his office) does not need to learn how to maintain the electrodes or the pump, or keep reagents on hand to refill reagent containers (a procedure which also carries with it the possibility of the introduction of contaminants, or the refilling of a container with the wrong reagent.)

Another advantage of the apparatus of the invention is that the disposable cartridge obviates expensive, time-consuming, and potentially contaminant-introducing preventive maintenance involved in the cleaning and/or replacement not just of reagents but also of the sensors, tubing, and other flow path elements, which would otherwise need to be kept in stock to be available when needed, and which would require, for servicing, the ready availability of trained service personnel, to both recognize the need for, and provide, such servicing.

An additional advantage of the apparatus of the invention is that the short, nearly horizontal flow path of the disposable cartridge prevents the development of a fully laminar flow path, which could otherwise result in measurement errors.

Other features and advantages of the invention will be apparent from the following description of the preferred embodiment thereof, and from the claims.

DESCRIPTION OF THE PREFERRED EMBODIMENT

The drawings will first briefly be described.

DRAWINGS

FIG. 1 is a diagrammatic representation of measurement apparatus of the invention;

FIG. 2 is a plan view of the top and bottom portions of apparatus of the invention;

FIG. 3 is a bottom plan view of a portion of the apparatus of FIG. 2;

FIGS. 4 and 5 are side sectional views of portions of said apparatus;

FIG. 8 is a perspective view of an electrode assembly of said apparatus.

STRUCTURE

Figure 5:
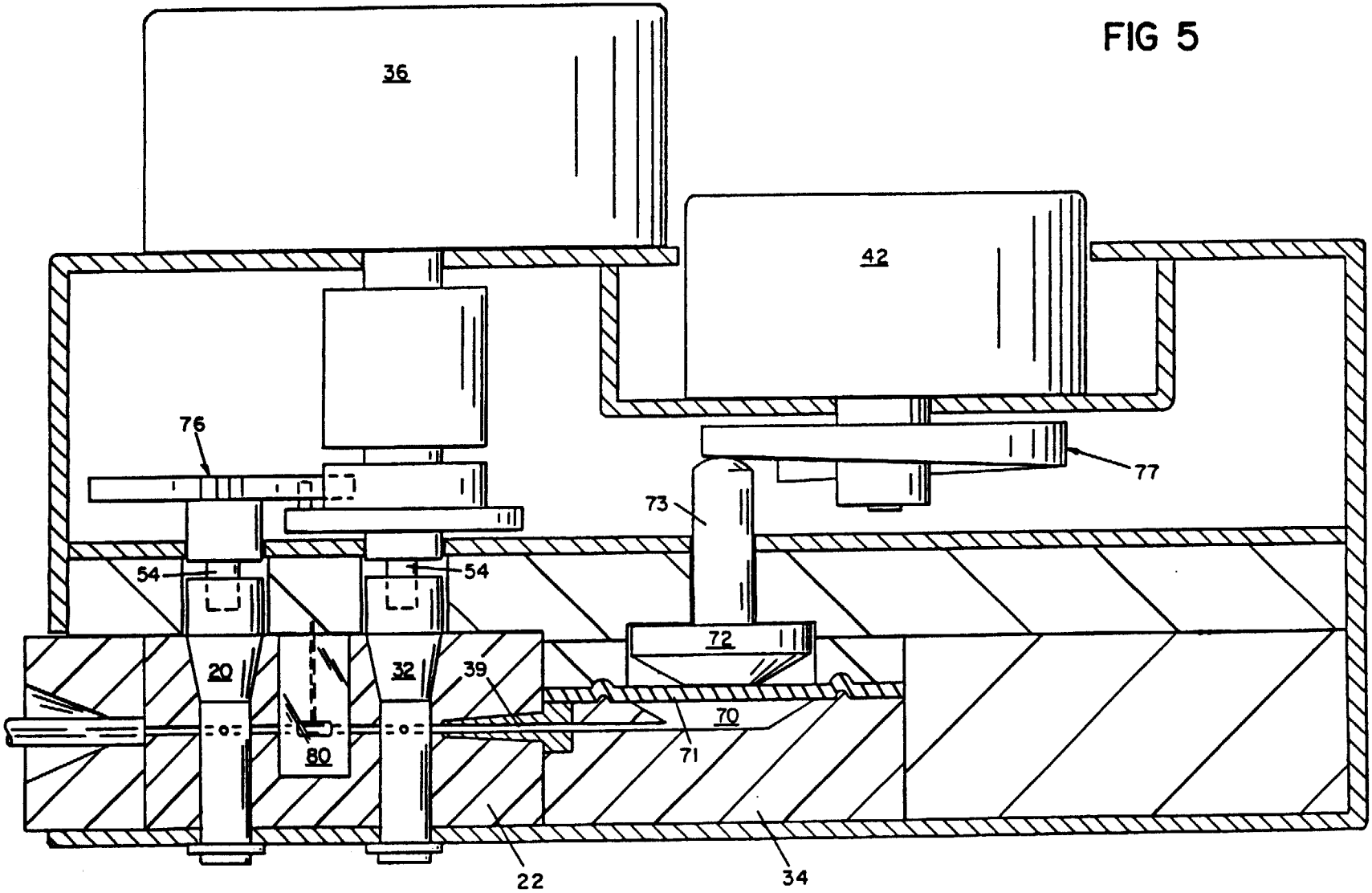

Referring to FIG. 1, analyzing apparatus 10 includes first module 12, connected to second module 14 such that module 12, a disposable cartridge, can be replaced periodically.

First module 12 contains a sample flow passage including, beginning upstream, sample inlet port 18; photosensor 49; flow cell 22, containing electrodes 24; and waste chamber 26. Reagent holding chambers 28 and 29 communicate with rotary selector valve 20 via passages 30 and 31. Flow cell 22 also includes, downstream from electrodes 24, rotary valve 32 which communicates with pump 34 via passage 39, and with reference chamber 78 via passage 37.

Second module 14 includes valve motor 36, computer 38 associated with display screen 40, and pump motor 42. Valve motor 36 is operatively connected to valves 20 and 32, via activator shafts 54. Pump motor 42 is operatively connected to pump 34 via pump cam 77. Electrodes 24 and reference chamber 78 are connected to computer 38 via electrical connections 48, and motors 36 and 42 are connected to computer 38 via electrical connections 50 and 52, respectively.

Referring now to FIG. 2, there is shown apparatus 10 taken apart, as when module 12 is to be replaced; the top portion of module 14 (containing the motors and computer) is shown in plan topside down, and module 12 and the bottom portion of module 14 (serving as a holder for module 12) are shown in plan. Module 12 fits into the bottom portion of module 14 such that the flat surface of each is flush with the other. The top portion of module 14 fits onto the bottom cartridge holder portion via snap connector posts 17, which mate with holes 15. Valve shafts 54 mate with valves 20 and 32.

Module 12 also includes vent 13 and six electrical connections 19, which meet pogo pin connections 100 in the top of module 14. As shown in FIG. 2, two of the connections are connected to contact points 82 from the two electrodes of the electrode assembly (FIG. 8) via wires 33; one to silver/silver chloride wire 43 from reference chamber 78; and three to the connection 47 to photosensor 49 at the entrance to flow passage 18. Module 12 further includes reagent inlet tubes 56 and 58 from reagent chambers 28 and 29, respectively; waste tube 64, leading to waste chamber 26 (which contains a disinfectant); reference tube 65 leading to reference chamber 78; and pump tube 45, leading to pump 34 (FIG. 1). Four vent tubes 51 connect chambers 28, 29, 26, and 78 with vent 13. Also shown is diaphragm 71 of pump 34. Slot 21 is large enough to permit the finger of the user to reach into module 14 to remove module 12 and then insert its identical replacement.

FIG. 3 is a bottom plan view of module 12, showing reagent chambers 28 and 29, reference liquid chamber 78, and waste chamber 26, surrounding the other three chambers.

FIG. 4 is a side sectional view of module 12, showing the positioning of the chambers below the remainder of the module.

FIG. 5, a side sectional view of apparatus 10 above the level of the reagent chambers and through the center of the flow passage, illustrates the relationship between motors 36 and 42 of module 14, and flow cell 22 and the remaining portion of the flow passage of module 12. Motor 36 drives Teflon and plastic rotary valves 20 and 32 via 3-poition, 45° Geneva mechanism 76, connected to the valves via valve shafts 54.

Motor 42 is connected via pump cam 77 to pump 34, which is made up of shaft 73, plunger 72, flexible diaphragm 71, and pump chamber 70; shaft 73 and plunger 72 are components of module 14, while diaphragm 71 and chamber 70 are components of module 12. Motors 42 and 36 are both Cannot PF55 series stepping motors. Flow cell 22, which is cast of flexible silicone rubber, makes nipple connection 39 with the remainder of module 12, at the point of continuation of the flow passage.

Figure 6:
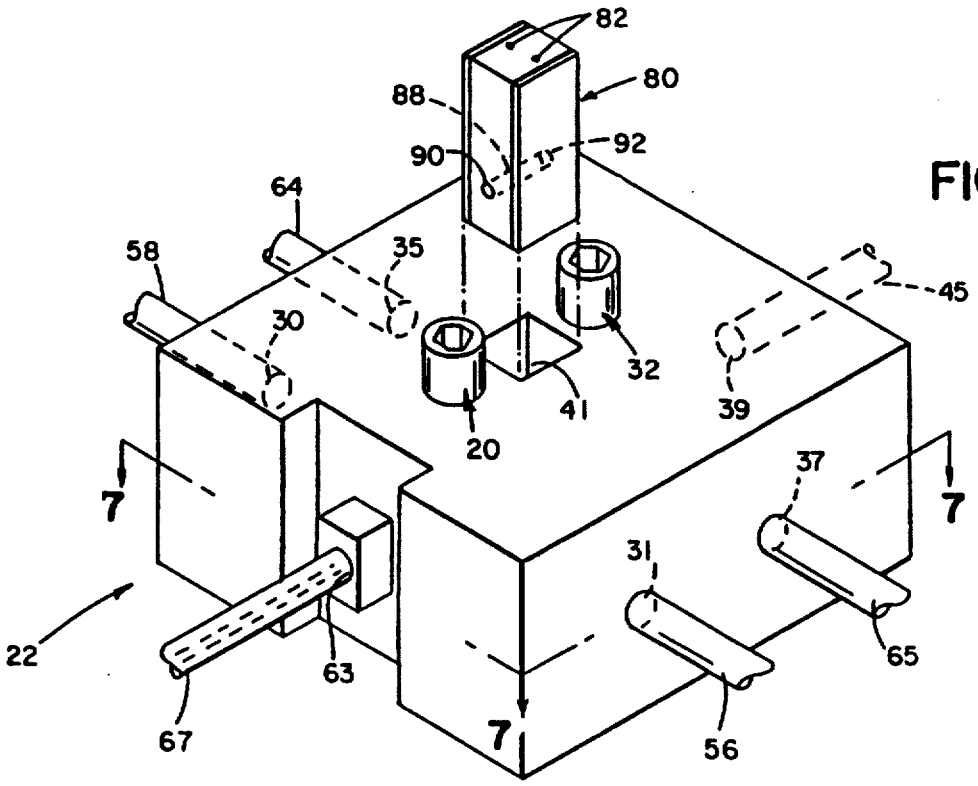
FIG. 6 is a perspective view of a portion of said apparatus.

FIG. 6 illustrates flow cell 22 and its connection to the remainder of apparatus 10. Slot 41 holds electrode assembly 80 (FIG. 8). All tubes mate with openings in flow cell 22 via nipple connections. Opening 63 is adapted to receive glass capillary tube 67.

Figure 7:
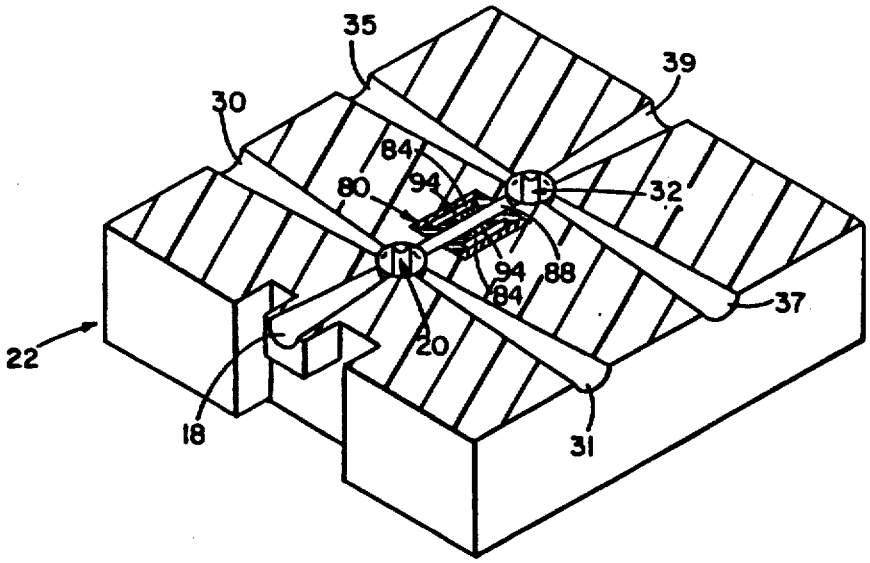
FIG. 7 is a sectional view taken at 7—7 of FIG. 6.

FIG. 7, taken at 7—7 of FIG. 6, shows passages of flow cell 22, including the upstream (19) and downstream (39) portions of the flow passage, reagent passages 30 and 31, waste passage 35, and reference passage 37.

Referring to FIG. 8, molded polyvinylchloride (PVC) electrode assembly 80 includes electrical connection points 82, connected to silver/silver chloride electrode wires 81 in the electrolyte solution of each electrode; two recessed, electrolyte-containing chambers 84; covered with flat, ultrasonically welded plastic plates 86; flow passage 88, including a sensor section including inlet and outlet ports 90 and 92, respectively; and integrated cast PVC, potassium ion selective and sodium ion selective membranes 94 flush with the remainder of the flow passage. The potassium ion selective membrane was made generally as described in Mikrochim, Acta (1980) Vol. II, page 309, and the sodium ion selective membrane was made generally as described in Auber et al. (1983) Clin. Chem. 29(8), 1508.

OPERATION

Referring to the Figures, to analyze a blood sample for potassium and sodium concentration, the sample is placed in capillary tube 67, which is inserted into the apparatus, triggering photosensor 49, which activates computer 38, which has been programmed to activate motors 36 and 42 to automatically take the sample through one measuring cycle, and to receive and process generated data. The computer and its software are not included in the present invention. In the illustrated embodiment, they are shown contained in module 14; they could just as well be in a separate module electrically connected to module 14.

The potassium and sodium ion concentrations of calibration reagent 28, sample, and calibration reagent 29, are measured sequentially. Each liquid is drawn into the flow path to contact the electrodes by the action of valves 20 and 32, and of pump 34. Motor 36, through Geneva mechanism 76, drives both valve 20, the position of which determines whether the sample, calibration reagent 28, or calibration reagent 29 enters the flow cell, and valve 32, the position of which determines the flow cell's communication with the pump, the reference chamber, and the waste chamber. The pump determines fluid volume in the flow cell, and moves up and down mechanically independently of the valves.

The electrochemical potentials of the sample and the calibration reagents are determined with reference to the reference liquid which, prior to each measurement, meets the liquid being analyzed in the downstream region 39 of the flow passage to create a liquid junction. The generated signals (electrical potentials) are then amplified and digitalized via an analog/digital converter; the activity of each ion is automatically calculated using the Nicolsky equation.

The first step in the process is a calibration analysis of the calibration reagent 28 remaining in the flow passage from the previous measurement; this is an isotonic sodium and potassium chloride reagent. After this measurement has been made, the sample fills the flow passage and is analyzed. Next, sodium and potassium chloride calibration reagent 29 enters and is analyzed, and then additional calibration reagent 28 enters and is analyzed, and remains for the start of the next cycle.

The measurements of the two calibration reagents serve to calibrate the electrodes, to act as a check on instrument functions, and to flush the system between samples. The salt solutions in chambers 28, 29, and 78 are all standard solutions used for these purposes by persons of ordinary skill in this field; their composition and method of preparation are given in Osswalt et al. page 74, in Lubbers et al. (1981).

PROGRESS IN ENZYME AND ION SELECTIVE ELECTRODES (Springer-Verlag).

Each liquid, after is has been analyzed, is ejected to waste chamber 26. As reagents and reference solution are depleted, air enters the chamber via vent 13; each chamber (i.e. chambers 26, 28, 29, and 78) is separately vented.

After a predetermined number of samples have been analyzed (when reagents have been exhausted), the user opens the top of module 14, reaches into opening 21, lifts out module 12, discards it, drops in a replacement module 12, and closes the top portion of module 14. Valve shafts 54 reversibly mate with valves 20 and 32, and electrical contact points 19 make contact. At this point, the apparatus is ready for use, with none of the components which contact the sample having been retained, cleaned, serviced, or touched by the user.

OTHER EMBODIMENTS

Other embodiments are within the following claims.

For example, the number of measurements made on each sample can be as low as one, or there can be measurement of considerably more than two chemical entities. Measurements of different chemical entities can be carried out at the same point in the flow passage, as in the above-described embodiment, or sequentially along the flow passage. Any chemical measurements can be made, using any chemical sensors; in addition to ion selective electrodes, measurements can be made using, e.g., pH electrodes, enzyme electrodes, or antibody/antigen sensors. Any liquid sample can be analyzed, e.g., urine, cerebrospinal fluid, industrial effluents, or drinking water. Any pump configuration can be used, e.g., peristaltic roller pumps, and the pump means can be located anywhere in the flow path, e.g., upstream rather than downstream from the sensor. One, rather than two, calibration reagents, can be used, and in some instances more than two or no calibration reagent will be required. The module containing the motors can be of any suitable configuration, e.g., all one piece, or two hinged parts. Any other valves, including check, poppet or squeeze valves, can be used; and any actuating means, e.g., other motors, electromagnetic actuators such as solenoids, or spring arrangements, can be used. Each valve and the pump can be driven by its own actuator, or one actuator can be used to drive all of them.

What is claimed is:

1. Apparatus for measuring or detecting a chemical entity in a liquid sample, said apparatus comprising a first module operationally connected to a second module, said first module comprising a flow passage for receiving at least one liquid sample and having reagent containing means, of sufficient size with sufficient reagent to [mix with] *analyze* a plurality of samples entering said flow passage to allow for successive analysis of a [plurlaity] *plurality* of samples, and having flushing fluid containing means said flow passage including a sensor section including sensor means for contacting fluid comprising a liquid sample [and] *or* reagent to measure or detect a chemical entity of the fluid while establishing a noncontaminating relationship with said second module and said first module including pump means for advancing the sample along said flow passage and actuating said flushing fluid containing means, thereby flushing said first module between analysis of successive samples, said second module comprising means for actuating said pump means, said second module being connected to said first module via connecting means permitting disconnection of said first module from said second module and connection of a replacement first module to said second module, and wherein *said* first module is in the form of a sealed disposable cartridge.

2. The apparatus of claim 1 wherein said sensor means of said first module comprises a plurality of different sensors for measuring a plurality of different chemical entities in a sample.

3. The apparatus of claim 1 wherein said pump means is located downstream from said sensor section.

4. The apparatus of claim 1 wherein said first module includes, downstream from said sensor section, a waste chamber for holding a sample after said chemical entity in the sample has been detected or measured.

5. The apparatus of claim 1 wherein said apparatus further comprises at least one reference chamber containing sufficient reference solution for analysis of a plurality of samples.

6. The apparatus of claim 1 wherein said flow passage of said first module includes, upstream from said sensor section, a sample inlet port for introducing the liquid sample into said first module.

7. The apparatus of claim 6 wherein said flow passage includes, downstream from said sample inlet port and upstream from said sensor section, a selector valve for controlling the intake of a sample into said flow passage, and wherein said second module includes means for actuating said selector valve.

8. The apparatus of claim 7 wherein said first module further comprises a holding chamber for holding a calibrating reagent, said holding chamber being connected to said flow passage, and passage of said calibrating reagent into said flow passage being controlled by said selector valve.

9. A replaceable module in the form of a disposable cartridge for use in apparatus for measuring or detecting a chemical entity in a liquid sample that establishes a non-contaminating relationship with said apparatus, said replaceable module comprising a flow passage for receiving at least one liquid sample, and having reagent containing means of sufficient size with sufficient reagent to [mix with] *analyze* a plurality of samples entering said flow passage to allow for successive analysis of a plurality of samples, and having a flushing fluid containing means, and wherein said flow passage includes a sensor section including sensor means for contacting fluid comprising a liquid sample [and] *or a* reagent, allowing for measuring or detecting a chemical entity of the fluid, said module including pump means for advancing the sample along said flow passage and actuating said flushing fluid containing means, thereby flushing said module between analysis of successive samples.

* * * * *